(12) United States Patent
Miyamoto

(10) Patent No.: US 8,508,620 B2
(45) Date of Patent: Aug. 13, 2013

(54) PORTABLE TERMINAL CAPABLE OF PRESENTING IMAGES BASED ON TIME

(75) Inventor: Atsushi Miyamoto, Tokyo (JP)

(73) Assignee: NEC Corporation, Tokyo (JP)

( * ) Notice: Subject to any disclaimer, the term of this patent is extended or adjusted under 35 U.S.C. 154(b) by 746 days.

(21) Appl. No.: 12/528,398

(22) PCT Filed: Jan. 30, 2008

(86) PCT No.: PCT/JP2008/051885
§ 371 (c)(1),
(2), (4) Date: Aug. 24, 2009

(87) PCT Pub. No.: WO2008/102642
PCT Pub. Date: Aug. 28, 2008

(65) Prior Publication Data
US 2010/0053373 A1    Mar. 4, 2010

(30) Foreign Application Priority Data

Feb. 24, 2007    (JP) ................................ 2007-044772

(51) Int. Cl.
*H04N 5/76* (2006.01)
*H04N 5/222* (2006.01)

(52) U.S. Cl.
USPC ................................... 348/231.5; 348/333.02

(58) Field of Classification Search
USPC ............................................. 348/231.5, 239
See application file for complete search history.

(56) References Cited

U.S. PATENT DOCUMENTS

| 7,325,198 | B2 * | 1/2008 | Adcock et al. ................. 715/722 |
| 7,636,733 | B1 * | 12/2009 | Rothmuller .................... 382/305 |
| 7,752,573 | B2 * | 7/2010 | Shiba et al. .................... 715/835 |
| 7,787,042 | B2 * | 8/2010 | Nagata ....................... 348/333.11 |
| 7,865,840 | B2 * | 1/2011 | Matsuzawa et al. .......... 715/808 |

(Continued)

FOREIGN PATENT DOCUMENTS

| CN | 1503555 A | 6/2004 |
| CN | 1610384 A | 4/2005 |

(Continued)

OTHER PUBLICATIONS

International Search Report for PCT/JP2008/051885 mailed Apr. 1, 2008.

(Continued)

*Primary Examiner* — Ngoc-Yen Vu

(57) ABSTRACT

A controller of a cellular phone acquires data of a date and a time when an object is captured from a clock part, in addition to image data of the object captured in an image capture mode by a camera part, and stores those data as image capture date data and image capture time data in a storage part in association with the image data in addition to the image data. Furthermore, when image capture date data of the image data stored in the storage part match date data outputted from the clock part in a standby mode, then the controller reads the image data and the image capture date and the image capture time corresponding to the image data from the storage part and controls a display part to display the image data with superimposing the image capture date and the image capture time thereon. The image data is displayed on the display part while the image capture date and the image capture time corresponding to the image data are superimposed on the image data.

5 Claims, 3 Drawing Sheets

(56) References Cited

U.S. PATENT DOCUMENTS

| | | | |
|---|---|---|---|
| 2005/0105374 A1* | 5/2005 | Finke-Anlauff et al. | 365/232 |
| 2007/0067342 A1* | 3/2007 | Haralambopoulos et al. | 707/104.1 |
| 2008/0016451 A1* | 1/2008 | Funabashi et al. | 715/757 |
| 2008/0046831 A1* | 2/2008 | Imai et al. | 715/765 |

FOREIGN PATENT DOCUMENTS

| | | | |
|---|---|---|---|
| JP | 2001-274936 A | | 10/2001 |
| JP | 2002-300241 A | | 10/2002 |
| JP | 2004-220420 A | | 8/2004 |
| JP | 2005-191979 | * | 7/2005 |
| JP | 2005-191979 A | | 7/2005 |
| JP | 2006-191444 A | | 7/2006 |
| JP | 2006-197109 A | | 7/2006 |
| JP | 2006-319561 A | | 11/2006 |
| JP | 2007-043727 A | | 2/2007 |

OTHER PUBLICATIONS

Chinese Office Action for CN 200880003843 dated Dec. 7, 2010.

* cited by examiner

PORTABLE TERMINAL CAPABLE OF PRESENTING IMAGES BASED ON TIME

This application is the National Phase of PCT/JP2008/051885, filed Jan. 30, 2008, which is based upon and claims priority from Japanese patent application No. 2007-44772, filed on Feb. 24, 2007, the disclosure of which is incorporated herein in its entirety by reference.

TECHNICAL FIELD

The present invention relates to a portable terminal such as a cellular phone, and more particularly to a portable terminal having an image capture function.

BACKGROUND ART

There have been provided various types of portable terminals having an image capture function. Atypical example of those portable terminals is a cellular phone.

A cellular phone having an image capture function includes a camera part operable to capture an image of an object and outputting image data, a clock part operable to measure and output a year, a month, a day, and a time of day, a display part operable to display the image data and the like, a controller, and the like. The controller is operable to store the image data acquired by the camera part and the year-month-day data and the time-of-day data from the clock part in the storage part. Furthermore, when the controller displays the stored image data on the display part, it superimposes the year, month, and day of image-capturing or the like on the image data.

For example, when an information terminal disclosed in Patent Document 1 (Japanese laid-open patent publication No. 2001-274936) receives captured image data transmitted from another information terminal and stores the image data in a flash memory, it also stores information on the date and time of receipt. When the image data are displayed on a display part, the information terminal superimposes the information of the date and time of receipt on the captured image data.

Patent Document 2 (Japanese laid-open patent publication No. 2004-220420) discloses an image retrieval method capable of retrieval and display of images stored in a storage part with use of information on a date and a time. Patent Document 3 (Japanese laid-open patent publication No. 2006-191444) discloses an image capture apparatus that allows a user to input a title of an image so that the user can readily recognize what was captured when the image is played back at a later time.

By combining the technology disclosed in Patent Documents 1 to 3 with each other, it is possible to superimpose some data, such as a date and a time outputted from a clock part, on image data obtained by capturing an image with a camera part, or to retrieve desired image data using some data, such as a date and a time, and then display the image data along with the data such as the date and the time.

DISCLOSURE OF INVENTION

Meanwhile, it is difficult to recall activities conducted several months ago, a year ago, or several years ago. For example, it is difficult to recall activities that transpired in the past, such as where one traveled one year ago, what special day was one year ago, or what one did on that day.

According to the inventions disclosed in the above Patent Documents, it is also necessary to retrieve image data stored in a storage part with use of a year, a month, and a day, or the like in order to recall the then activities. Such retrieval operation is so troublesome that a user rarely performs the retrieval operation to view past image data. Thus, although captured images are stored as data, they are unlikely to be used to recall user's past activities. As a result, there is a problem that the image data are not effectively utilized.

An object of the present invention is to display image data that were captured in the past in a comprehensible manner with a simple operation in order to allow a user to readily recall his/her past activities, anniversaries, or the like.

Furthermore, another object of the present invention is to effectively utilize image data that was captured in the past.

A portable terminal according to the present invention comprises an image capture part operable to capture an image of an object in an image capture mode and output image data, a clock part operable to measure a present date and a present time, a controller, a storage part, a display part, and a communication part operable to perform communication and to stand by for receiving data in a standby mode. According to an aspect of the present invention, the controller is operable to acquire image data of the object captured in the image capture mode by the image capture part, to acquire, from the clock part, data of a date and a time when the object is captured by the image capture part, and to store the data of the date and the time respectively as image capture date data and image capture time data in the storage part in association with the image data in addition to the image data. The controller is also operable to perform a retrieval in the standby mode to determine whether image capture date data of the image data stored in the storage part match date data outputted from the clock part, and to read, from the storage part, the image data corresponding to the matched image capture date data and the image capture date and the image capture time corresponding to the image data and control the display part to display the image data with superimposing the image capture date and the image capture time thereon if it is determined that there are matched data.

According to the present invention, image data that were captured in the past can be displayed in a comprehensible manner with a simple operation, so that a user can readily recall his/her past activities, anniversaries, or the like. Furthermore, image data that was captured in the past can effectively be utilized.

BEST MODE FOR CARRYING OUT THE INVENTION

A portable terminal according to an embodiment of the present invention will be described below.

Figure 1:
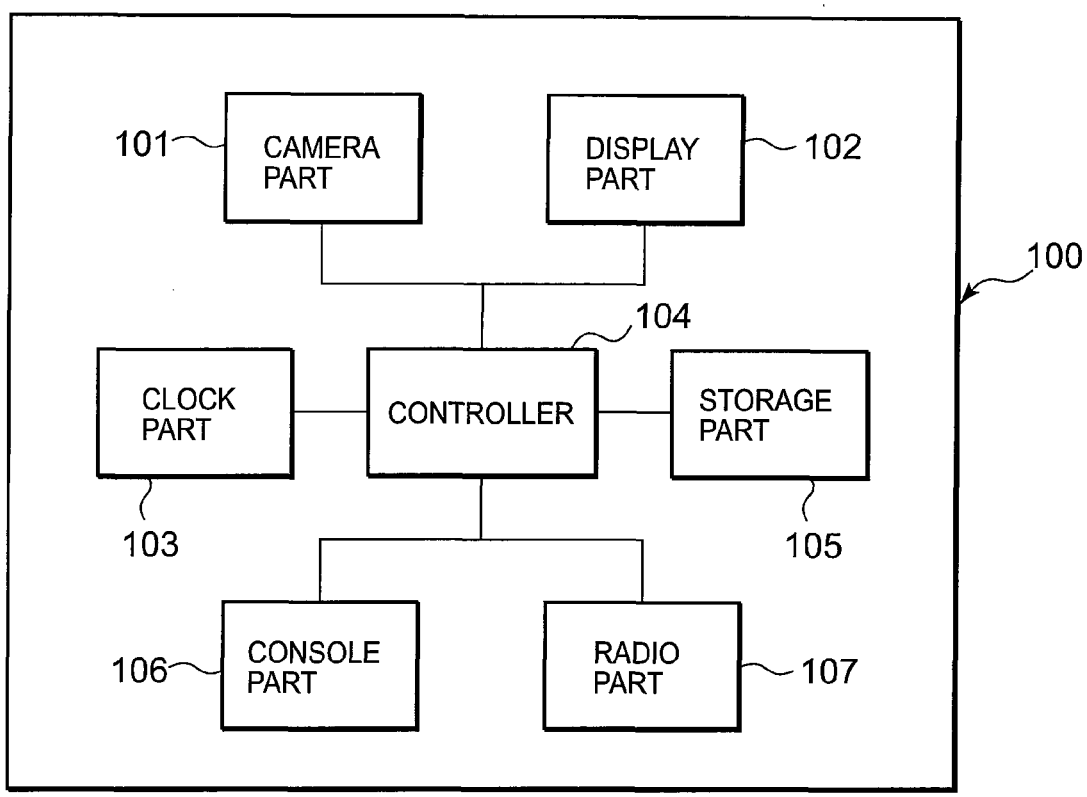
FIG. 1 is a block diagram of a portable terminal according to an embodiment of the present invention.

FIG. 1 is a block diagram of a portable terminal according to an embodiment of the present invention, which shows an example of a cellular phone.

In FIG. 1, a cellular phone 100 as a portable terminal comprises a camera part 101, a display part 102, a clock part 103, a controller 104, a storage part 105, a console part 106, and a radio part 107.

The camera part 101 is operable to capture an image of an object and has an image capture function for moving images or still images. The camera part 101 is operable to output image data corresponding to a captured image. The display part 102 is operable to display an image captured by the camera part 101 or other information. The clock part 103 is operable to measure a year, a month, a day, and a time of day and transmit values of the date and the time or the like to the controller 104. The controller 104 comprises a central processing unit (CPU) operable to control operation of each component of the cellular phone 100.

The storage part 105 is operable to store therein image data obtained by capturing an image, a control program to be executed by the controller 104, and the like. The console part 106 includes a ten-key pad or a cursor keypad and is operable to receive an operational input from a user. The radio part 107 is operable to perform a communication process with a radio base station in a case where the cellular phone 100 is used as a communication device. The aforementioned hardware components can be implemented by technology equivalent to existing cellular phones, and the details of those components are omitted herein.

The camera part 101 and the radio part 107 may be referred to as an image capture part and a communication part, respectively.

Figure 2:
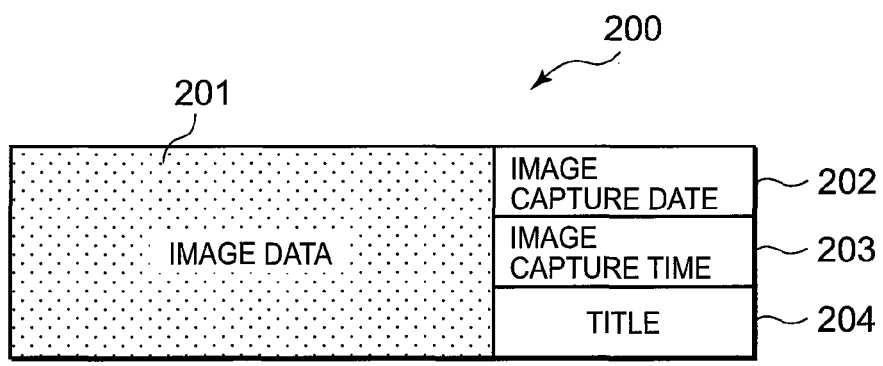
FIG. 2 is a diagram showing an example of captured image data of a portable terminal according to the embodiment of the present invention.

FIG. 2 shows an example of captured image data 200 obtained in the cellular phone 100 according to the embodiment of the present invention. In the captured image data 200, the image data 201 outputted from the camera part 101 are associated with a date of the image capture (image capture date) 202 and a time of the image capture (image capture time) 203 outputted from the clock part 103 and with a title of the image 204 inputted from a character input part of the console part 106 by a user. The date 202 of the captured image data 200 includes information on a year, a month, and a day. However, the date 202 of the captured image data 200 may properly be configured such as to include only a month and a day or include only a day.

Figure 3:
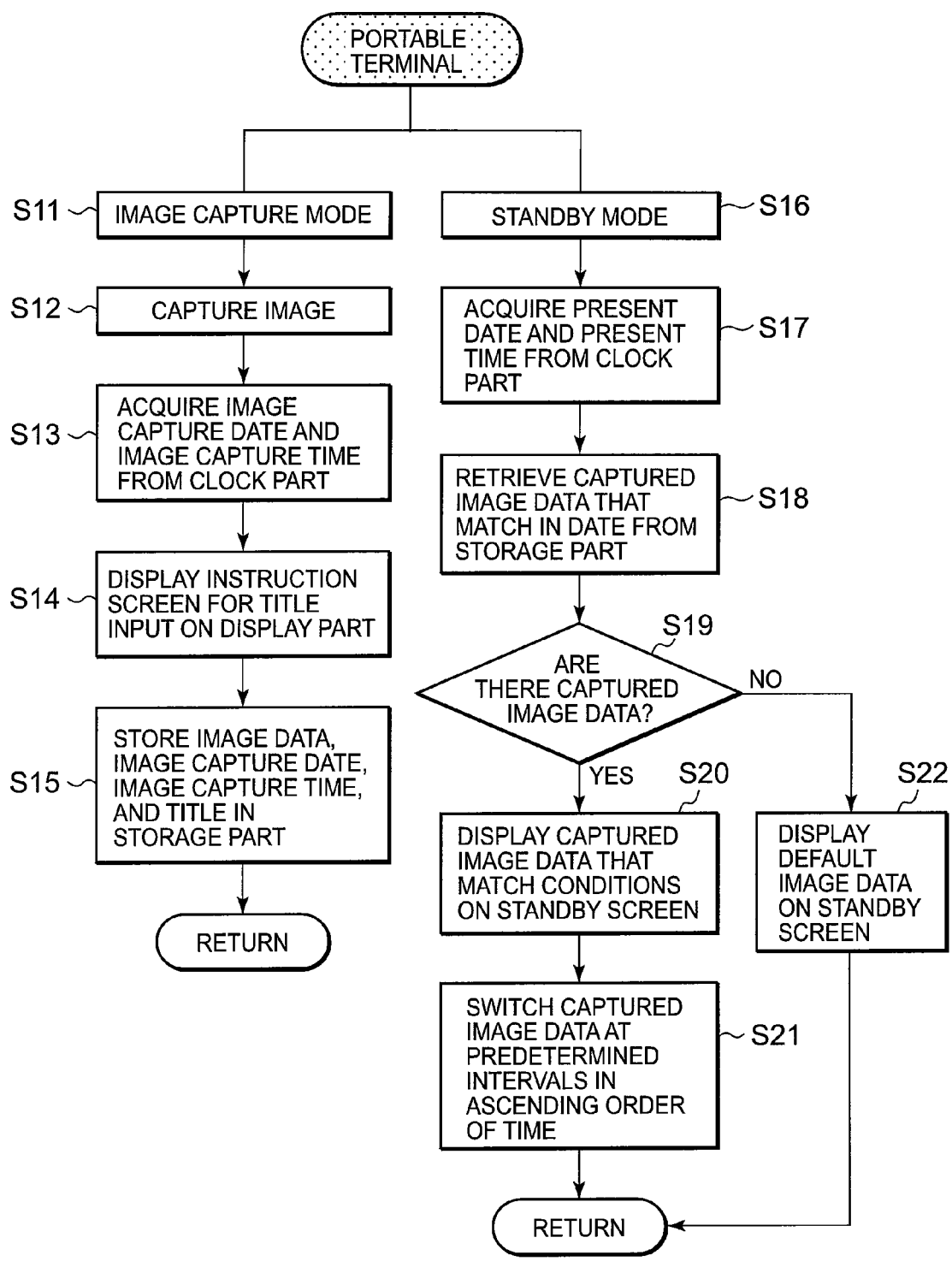
FIG. 3 is a flow chart explanatory of operation of a portable terminal according to the embodiment of the present invention.

FIG. 3 is an operational flow chart of the cellular phone 100 according to the embodiment of the present invention. The cellular phone 100 can be put in an image capture mode that captures an image of an object or in a standby mode for radio communication. When the cellular phone is started up, it is put into the standby mode as with existing cellular phones. The cellular phone 100 is put into the image capture mode by user's operation. When the image capture mode is terminated, the cellular phone is put into the standby mode again.

Figure 4A:
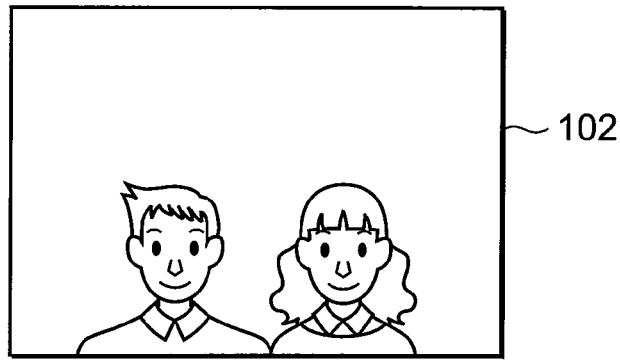
FIG. 4A is a diagram showing an example of a display image of a portable terminal according to the embodiment of the present invention.
Figure 4B:
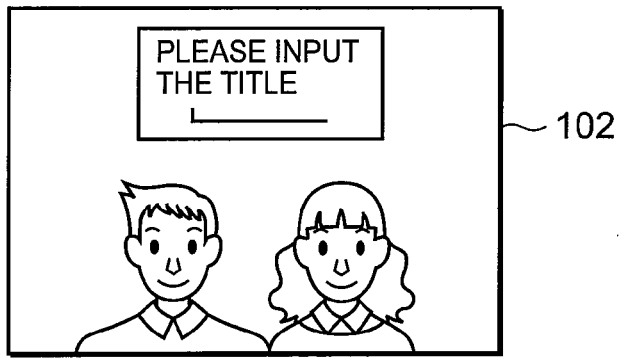
FIG. 4B is a diagram showing an example of a display image including instructions to input a title of the displayed image of FIG. 4A.
Figure 4C:
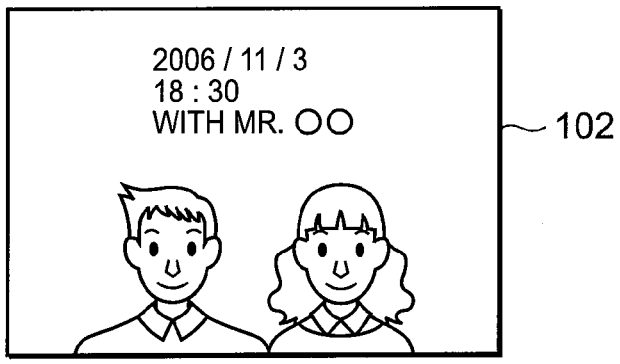
FIG. 4C is a diagram showing an example in which a display image including the title inputted in FIG. 4B is displayed on a standby screen.

FIGS. 4A to 4C show examples of images displayed on the display part 102. FIG. 4A shows a display example of captured image data, FIG. 4B shows a display example instructing a user to input a title of the display shown in FIG. 4A, and FIG. 4C shows a display example in which the cellular phone is in the standby mode.

Operation of the cellular phone 100 according to the embodiment of the present invention will be described below with reference to FIGS. 1 to 3 and 4A to 4C. First, the image capture mode will be described.

In FIG. 3, when the controller 104 of the cellular phone 100 detects that a user has made a predetermined operation for transition to the image capture mode with use of the console part 106, then the controller 104 puts the cellular phone 100 into the image capture mode (Step S11) and controls the camera part 101 so that the camera part 101 captures an image of an object in response to a user's operation of a predetermined button on the console part (e.g., pushing a shutter button down) (Step S12).

When the controller 104 receives, from the camera part 101, image data obtained by capturing an image with the camera part 101, it controls the display part 102 to display the captured image thereon as shown in FIG. 4A and acquires a date and a time outputted from the clock part 103 (the present date and the present time) as an image capture date and an image capture time (Step S13).

Subsequently, the controller 104 controls the display part 102 to display instructions urging the user to input a title of the captured image as shown in FIG. 4B (Step S14). When the user inputs characters of the title with the console part 106 and pushes a set button down, the controller 104 stores the acquired image data, the image capture date, the image capture time, and the inputted title as captured image data 200 in the storage part 105 (Step S15).

Next, the standby mode will be described. When the cellular phone is put into the standby mode by a predetermined operation on the console part 106 (e.g., pushing a mode-switching button down) (Step S16), then the controller 104 acquires the present date and the present time from the clock part 103 in response to the predetermined operation of the user (Step S17).

Then the controller 104 retrieves captured image data corresponding to the image capture date (image capture date data) that matches the acquired date from among multiple sets of captured image data stored in the storage part 105 (Step S18). The date and the time outputted from the clock part 103 and the captured image data 200 include information on a year, a month, a day, and a time of day. Here, the controller 104 retrieves image data that match the acquired date in month and day. Nevertheless, the controller 104 may retrieve image data that match the acquired date in year, month, and day.

The controller 104 judges whether the captured image data that match the retrieval conditions have been stored in the storage part 105 (Step S19). If the captured image data that match the retrieval conditions have been stored in the storage part 105, then the controller 104 reads those data and controls the display part 102 to display those data as a standby image thereon (Step S20). At that time, the controller 104 controls the display part 102 to display the image data and superimpose the image capture date (the year, month, and day of the image capture in this example), the image capture time, and the title corresponding to those image data on the image data as shown in FIG. 4C.

When multiple sets of captured image data match the conditions, for example, when multiple images have been captured on the same day or when multiple images have been captured on the same date of past years, then the controller 104 controls the display part 102 to switch image data displayed on the standby screen at predetermined intervals in the order of the image capture date/time (Step S21). That order of the image capture date/time may be an ascending order of the image capture date or the image capture time, or a descending order of the image capture date or the image capture time. As a result, the standby screen as shown in FIG. 4C is switched at the predetermined intervals and displayed on the display part 102.

If no image data match the condition in Step S19, the controller 104 controls the display part 102 to display default image data of the cellular phone 100 (image data that have been stored as default data in the storage part 105) on a standby screen (Step S22). In this case, the default image is displayed on the display part 102.

In consideration of a case whether the standby mode continues for several days without transition from the image capture mode to the standby mode, retrieval of captured image data corresponding to an image capture date (image capture date data) that matches a date acquired from the clock part 103 may be performed once a day. The timing of the retrievals may be predetermined.

As described above, the cellular phone according to the embodiment of the present invention acquires, from the clock part 103, data of a date and a time when an image is captured by the camera 101 in an image capture mode, and stores those data respectively as image capture date data and image capture time data in the storage part 105 in association with the captured image data of the object in addition to the image data. Furthermore, the cellular phone is switched into a standby mode. When the image capture date data of the image data stored in the storage part 105 match date data outputted from the clock part 103, then those image data are automatically displayed while the image capture date and the image capture time corresponding to the image data are superimposed on the image data. Therefore, as described in connection with FIG. 4C, an image capture date or the like can be known merely by viewing an image displayed on the display part 102 without any special retrieval operation. Furthermore, since the image data that were captured in the past are displayed along with the image capture date or the like on the standby screen, the standby screen can remind a user of his/her past activities such as travels, anniversaries, and the like.

Furthermore, since the date, the time, and the title are superimposed on the image data, the image data that were captured in the past can be displayed in a comprehensible manner.

Moreover, the image data that were captured on a past day corresponding to the present date or the like can automatically be displayed on a standby screen based on the present date or the like.

In a case where a large number of sets of image data that were captured in the past are stored in the storage part 105, those image data can effectively be used.

The captured image data 200 may be viewed at any time by user's operation of a specific button, i.e., based on data of a date when the specific button is operated. In this case, the controller 104 may be configured such that an image capture date, an image capture time, and a title are superimposed on image data having a matched date. Nevertheless, only image data may be displayed depending upon the user's settings.

The present invention can be applied not only to image-capturing of still images, but also to image-capturing of moving images.

The present invention is applicable not only to a cellular phone, but also generally to portable terminals having an image capture function and a communication function, such as a PHS (Personal Handy-Phone System), a PDA (Personal Digital Assistant), or a laptop personal computer.

The invention claimed is:

1. A portable terminal comprising a console part having a character input function, an image capture part operable to capture an image of an object in an image capture mode and output image data, a clock part operable to measure a present year-month-day and a present time, a controller, a storage part, a display part, and a communication part operable to perform communication and to stand by for receiving data in a standby mode, wherein the controller is operable to acquire image data of the object captured in the image capture mode by the image capture part, to acquire, from the clock part, data of a year-month-day and a time when the object is captured by the image capture part, and to store the data of the year-month-day and the time respectively as image capture year-month-day data and image capture time data in the storage part in association with the image data in addition to the image data, and wherein the controller is also operable to perform a retrieval in the standby mode to determine whether image capture date data of the image data stored in the storage part match date data outputted from the clock part, and to read, from the storage part, the image data corresponding to the matched image capture date data and the image capture date and the image capture time corresponding to the image data and control the display part to display the image data with superimposing the image capture year-month-day and the image capture time thereon if it is determined that there are matched data, and wherein, when a user operates a specific button, the controller is also operable to perform a retrieval to determine whether the image capture date data or the image capture month-day data of the image data stored in the storage part match date data or month-day data at the time of the operation of the specific button, and to read, from the storage part, the image data corresponding to the matched image capture date data or the matched image capture month-day data and the image capture date or the image capture month-day and the image capture time corresponding to the image data and control the display part to display the image data with superimposing the image capture date and the image capture time thereon if it is determined that there are matched data.

2. The portable terminal as recited in claim 1, wherein the controller is operable to store a title character, inputted from the console part, in the storage part in association with the image data in addition to the image data, and to read, from the storage part, the title character corresponding to the image data when the image data stored in the storage part are to be displayed on the display part in the standby mode and control the display part to display the image data with superimposing the title character thereon.

3. The portable terminal as recited in claim 1, wherein, when multiple sets of image data including the image capture date data or the age capture month-day data that match the date data or month-day data outputted from the clock part are stored in the storage part, the controller is operable to control the display part to display the multiple sets of image data in an order of the image capture date/time.

4. The portable terminal as recited in claim 3, wherein the controller is operable to control the display part to display the multiple sets of the image data at predetermined intervals in the order of the image capture date/time.

5. The portable terminal as recited in claim 4, wherein the controller is operable to control the display part to display the multiple sets of the image data at the predetermined intervals in an ascending order of the image capture date/time.

* * * * *